United States Patent [19]

Baylis et al.

[11] 4,351,802
[45] Sep. 28, 1982

[54] HEADSPACE-SAMPLING APPARATUS

[75] Inventors: Michael A. Baylis, Totton; Peter Harris; Stewart R. Massey, both of Southampton, all of England

[73] Assignee: British-American Tobacco Co., Ltd., London, England

[21] Appl. No.: 191,028

[22] Filed: Sep. 26, 1980

Related U.S. Application Data

[63] Continuation of Ser. No. 14,607, Feb. 23, 1979, abandoned.

[30] Foreign Application Priority Data

Feb. 28, 1978 [GB] United Kingdom ............... 7920/78

[51] Int. Cl.³ ............................................. G01N 1/22
[52] U.S. Cl. .................................. 422/89; 73/864.83; 73/864.84
[58] Field of Search ........................ 422/89; 23/230 C; 73/864.82, 864.83, 864.84

[56] References Cited

U.S. PATENT DOCUMENTS

| | | | |
|---|---|---|---|
| 3,421,857 | 1/1969 | Reichle et al. | 422/89 |
| 3,730,002 | 5/1973 | Penton | 73/864.82 |
| 3,985,016 | 10/1976 | Haruki | 73/23.1 |
| 4,004,881 | 1/1977 | Ligon | 73/23.1 |
| 4,096,734 | 6/1918 | Khayat | 73/23.1 |
| 4,133,640 | 1/1979 | Clinton et al. | 23/230 PC |
| 4,185,500 | 1/1980 | Boser | 73/864.82 |
| 4,226,119 | 10/1980 | Boser | 73/864.82 |

Primary Examiner—William F. Smith
Attorney, Agent, or Firm—Kane, Dalsimer, Kane, Sullivan and Kurucz

[57] ABSTRACT

In a headspace-sampling apparatus and method, use is made of a sampling body which defines a sample chamber, first passage means extending from said chamber, means for connecting said passage means to the entry end of a chromatography column held in operative position in a gas chromatograph, second passage means extending to said chamber, and means for connecting a source of gas to said second passage means. When the first-named connection means is connected to the column, a gas flow can be established within the body from the second named connection means through the said chamber to the entry end of the column, whereby a headspace sample of said substance is swept directly from said chamber on to an entry end region of said column, the headspace sample being cumulatively trapped at said region.

6 Claims, 6 Drawing Figures

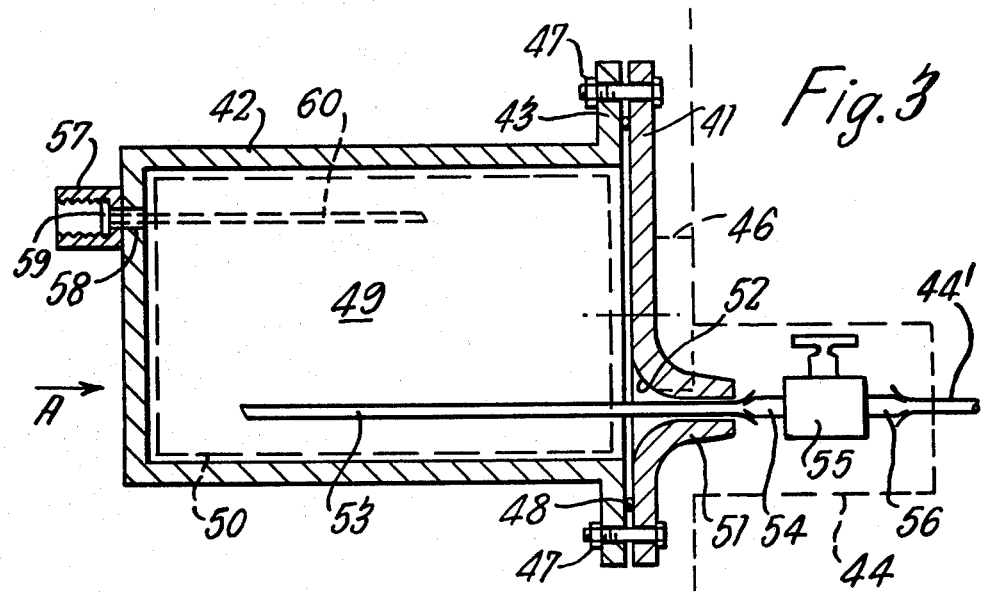
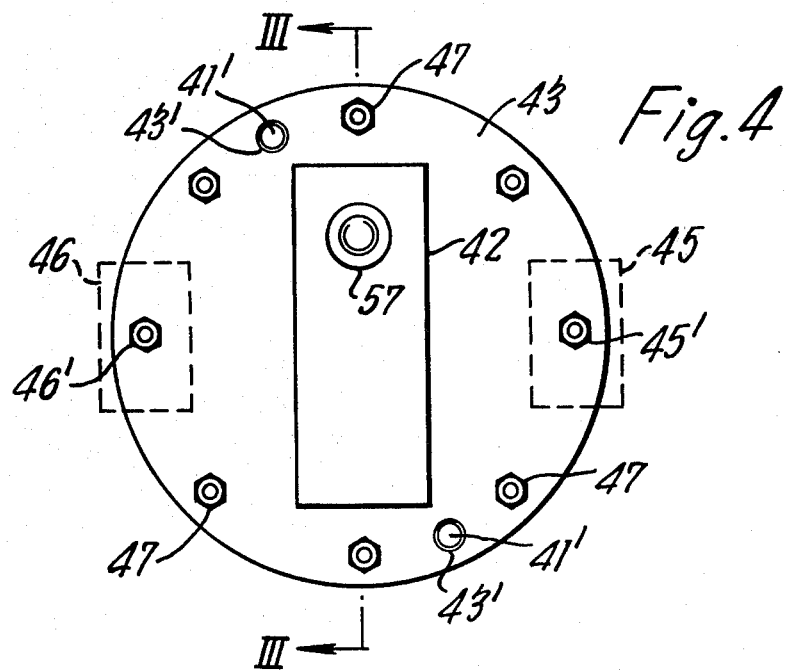

HEADSPACE-SAMPLING APPARATUS

This is a continuation of application Ser. No. 014,607, filed Feb. 23, 1979 now abandoned.

This invention relates to a headspace-sampling method and apparatus. Gas-chromatography headspace-analysis is a technique used in identifying volatile substances emanating from a solid or a liquid. A "headspace" may be the vapour space in a laboratory container, a vial say, into which the solid or liquid has been inserted, or it can be a vapour space within a packaging container, a cigarette packet or a paint tin for example. In carrying out this technique, it is necessary to transfer a sample of the vapour in the headspace to the chromatography column of a gas chromatograph.

Known methods of headspace sampling and the apparatus used for such methods have various disadvantages in practical use and it is an object of the invention to provide a headspace-sampling method and apparatus which allow effective sampling to be performed in a similar fashion without incurring disadvantages of the known methods.

In one known method, the solid or liquid material concerned, a body of tobacco for example, is held in a first container connected to a second container holding a solid adsorbent, carbon for example. A stream of stripping gas is swept over or through the material in the first container so as to carry volatile constituents of the material into the second container, where the adsorbent serves to adsorb them. After a time sufficient for the adsorption, the second container is disconnected from the first and connected to the column of a chromatograph in which the volatile constituents are subjected to thermal desorption. A disadvantage of this method is that the adsorbent may act, for example catalytically, upon the said constituents to promote chemical change resulting in artifact production. Chemical change may also take place when the volatile constituents are desorbed for transfer to the gas chromatograph. The adsorbent may be selective in the adsorption and/or desorption process. Furthermore, it is time consuming to adsorb and then desorb the volatile substances and, in some cases, artifact formation is time dependent. Finally, not all of the volatile substances carried by the gas may be trapped on the adsorbent and not all of these may be desorbed.

In another known method, the material is placed in a vial which is then pressurized by piercing a septum with a hollow needle connected to a source of inert gas. After pressurization, the needle is removed and, when equilibrium conditions have been allowed to become established within the vial, the pressurization of the vial is utilized for ballistic injection from the vapour space of the vial to the chromatography column of the gas chromatograph. For this purpose, the septum is pierced by a second needle in communication with the entry end of the column. The period of injection is very short (1–10 seconds) which limits the amount of volatile substances injected into the column.

In another known method using a vial, there is no pressurization of the vapour space thereof. Injection of a headspace sample into the chromatography column is by means of a syringe the needle of which is caused to penetrate a septum of the vial. After a sample has been drawn into the syringe, the needle is withdrawn from the vial and caused to penetrate a septum in the injection block of the gas chromatograph for transferring the sample to the column. The headspace sample drawn into the syringe is unavoidably subject to changes in volume and pressure and thus it is commonly observed, upon injection of the sample into the column, that some constituents of the sample condense in the syringe. Thus the vapour expelled from the syringe may not be representative of the headspace vapour within the vial.

It has also been proposed to introduce a headspace-vapour sample to a chromatography column by removing the whole column from the chromatograph and inserting the upstream end of the column into the neck of a flask holding the liquid or solid material. A stream of stripper gas is then caused to flow through the flask to the column at the upstream end of which cold-capture means is positioned. After the elapse of sufficient time, the end of the column is removed from the neck of the flask and the column is refitted in the chromatograph. This method of sampling, as well as being generally inconvenient, is time consuming, involving as it does the removal and re-fitting of the column. It thus presents the possibility of artifact formation. There is also a danger that the coolant, dry ice for example, used in the capture means may enter the column.

The present invention provides headspace-sampling apparatus comprising sampling body means which defines a sample chamber and which further comprises first passage means extending from said chamber, connection means for connecting said passage means to the entry end of a chromatography column held in operative position in a gas chromatography, second passage means extending to said chamber, and connection means for connecting a source of gas to said second passage means, whereby, when the first-named connection means is connected to the said column, a gas flow can be established within the said body means from the second named connection means through the said chamber to said entry end of the column.

Also according to the present invention, headspace-sampling apparatus comprises body means defining a sample chamber, first passage means extending from said chamber, means for mounting said apparatus on a gas chromatograph so that when the apparatus is so mounted said first passage means communicates with the entry end of a chromatography column held in an operative position thereof in said chromatograph, and second passage means extending to said chamber, the arrangement being such that when said apparatus is mounted on the chromatograph, a gas stream can be established from said second passage means to the column via said chamber and first passage means.

Preferably, the body means comprises a first part mountable on the chromatograph by the mounting means, and a second part releasably securable to the first part to permit the introduction of a sample into and its removal from the chamber.

Advantageously the apparatus comprises means for holding a hollow needle so that the needle extends within the sample chamber. In the use of the apparatus, it is then arranged that the needle penetrates an article positioned in the sample chamber, of which article a headspace is to be sampled. The article may, for example, be a cigarette or cigarette packet. The apparatus may also include provision for a further hollow needle to extend within the chamber, in which case, when the further needle is in place, the second passage means communicates with an entry end of the further needle, the arrangement being such that the further needle also penetrates the article in the chamber. The chamber may with advantage be of such form that when an article, a cigarette packet for example, is placed therein the outer peripheral surface or surfaces of the article lie closely against the inner wall or walls of the chamber.

Advantageously the apparatus may further comprise means for heating the sample chamber. The increase of temperature thus made possible will permit of larger sample amounts being supplied to the column, leading in turn to larger peaks on the chromatogram and aiding identification of individual peaks. An increase in temperature will also extend the range of detection to compounds of lower volatility.

In order that the invention may be clearly understood and readily carried into effect, reference will now be made, by way of example, to the accompanying diagrammatic drawings, in which:

FIG. 3 shows a sectional elevation, on line III—III of FIG. 4, of a second headspace-sampling apparatus, and FIG. 4 shows a partial end view in the direction of arrow A, of the apparatus of FIG. 3.

Figure 1:
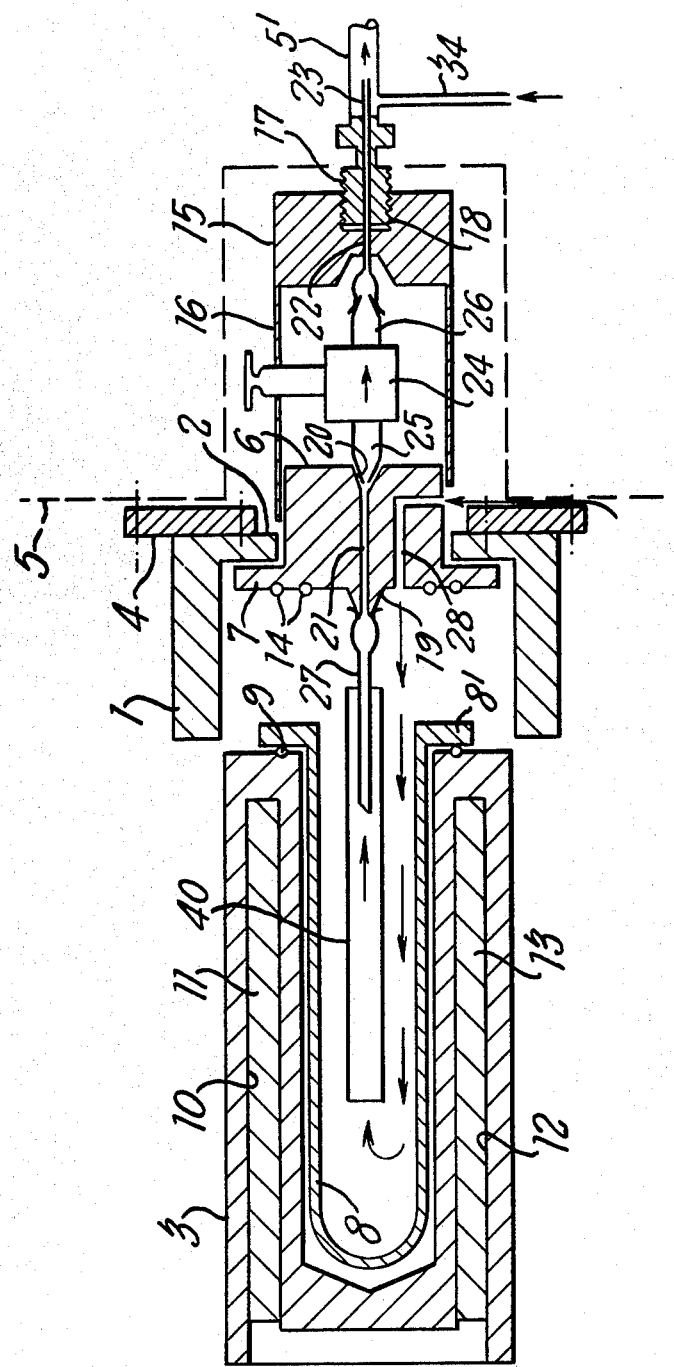
FIG. 1 shows, in axial section, a headspace-sampling apparatus mounted on a gas chromatograph.

The headspace-sampling apparatus shown in FIG. 1 comprises a first cylindrical body member 1 having an inwardly extending flange 2 at the right-hand end and a second cylindrical body member 3 which is closed at the left-hand end. Each of members 1 and 3 is made of aluminium.

Secured at the right-hand end of the member 1 is a mounting bracket 4, of heat-insulating material, by which that member is mounted on a gas chromatograph, of which parts are indicated in outline by broken lines 5. A cylindrical block 6 of heat-insulating material (that marketed under the Registered Trade Mark 'Teflon', for example) is received as a close fit in the opening defined by the flange 2. A flange 7 extending outwardly of the block 6 at its left-hand end is seated against the inner face of the flange 2. Clearance between the block 6 and flange 2, and other clearances in FIG. 1, have been exaggerated for the sake of clarity.

Received as a close fit in the body member 3 is a flanged sample tube 8 of glass. An 'O'-ring 9 provides for resilient seating of the flange 8' of the tube 8 on the right-hand end face of the member 3. Within the wall of the member 3 there extend, equi-angularly spaced about the axis of that member, three longitudinal pockets, in each of which an electrical cartridge heater is received. One of these pockets is shown at 10 with a heater 11 therein. A similar pocket 12 houses a temperature-measuring probe 13 associated with temperature-control means (not shown) operable, in response to signals from the probe 13, to control the heat output of the heaters 11, so as to maintain the temperature within the tube within ±1° C. of a selected value.

By moving the body member 3 to the right from the position shown in FIG. 1, a right-hand end portion thereof is received as a close fit in the member 1. The member 3 is releasably securable to the member 1 by bayonet fastenings (not shown) and, when it is so secured, two 'O'-rings 14 provide an hermetic seal between the block 6 and the flange 8' of the tube 8.

The apparatus further comprises a cylindrical aluminum block 15 having, integral therewith, a leftwardly extending cylindrical sleeve 16 of which a lefthand portion is received as a close fit on the block 6. The entry end of a chromatography column 5' of the chromatograph 5 is connected to the block 15 via an injection connector 17 screwed into a right-hand end portion of the block. Inwardly of the connector 17 a septum 18 is located in the block 15.

At its left and right-hand ends respectively, the block 6 is provided with a co-axial protrusion 19 and a co-axial recess 20. Extending axially of the block 6 is an open-ended narrow bore 21. The block 15 is similarly provided with an axial open-ended narrow bore 22. A hollow needle 23, of the nature of a syringe needle, extends from the left-hand side of the block 15 through the bore 22, septum 22, septum 18 and connector 17 to the interior of the entry end of the column 5' held in operative position in the chromatograph 5.

Within the sleeve 16 a three-way valve 24 is located between the blocks 6 and 15. A first connection limb 25 of the valve 24 is sealably received in the recess 20 in the block 6. A second limb 26 is sealably received in a bulbous left-hand end portion of the needle 23. A third limb 24' (FIG. 2—not seen in FIG. 1), which projects through an opening in the sleeve 16, includes a gas-flow restrictor 24" hereinafter mentioned.

A bulbous right-hand end portion of a further hollow needle 27 (FIG. 1) is sealably received on the protrusion 19 of the block 6. Thus the interior of the sample tube 8 can be placed in communication with the entry end of the column 5' via the needle 27, the bore 21 of the block 6, the three-way valve 24 and the needle 22.

A passage for the admission of stripper gas, suitably high purity nitrogen, to the sample tube 8 is provided in the form of a narrow bore 28 extending through the block 6.

As is usual the chromatograph is provided with means (not shown) for cooling and heating the column 5' and with a heatable injection block (also not shown).

Figure 2:
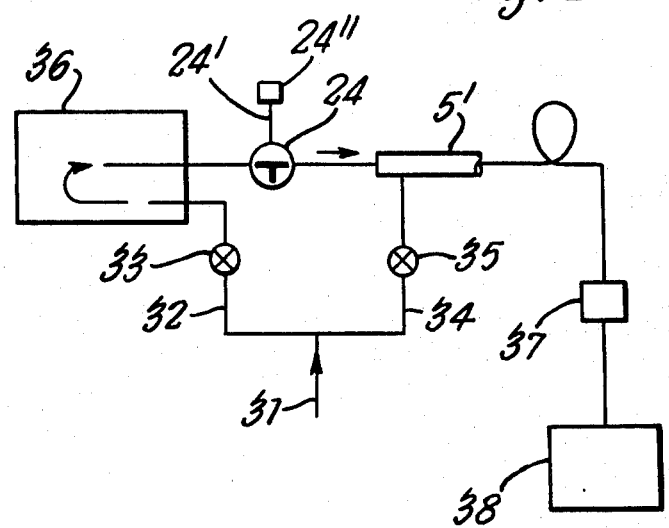
FIG. 2 shows gas-flow circuitry associated with the apparatus and chromatograph.

As shown in FIG. 2, the stripper gas can be supplied through line 31 from a source (not shown) to a line 32 provided with a valve 33 or to a line 34 with a valve 35. During head-space sampling, the valve 33 is open and the valve 35 closed so that stripper gas can flow through the line 32 and the bore 28 into the sampling apparatus, indicated at 36 in FIG. 2. In passing through the apparatus, this gas picks up volatile constituents from a product contained within the tube 8. During sampling, the three-way valve 24 is set (as indicated in FIG. 2) so that the gas flow is directed to the chromatography column 5', the volatile constituents being trapped at the entry end of the column by maintaining the column at a sub-ambient temperature. The effect of substantially complete adsorption can thus be achieved.

Figure 2A:
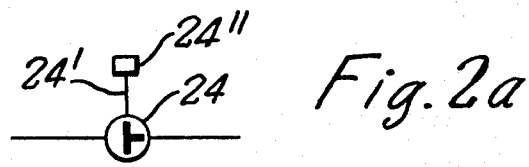
FIGS. 2a and 2b show respective settings of a three-way valve of the apparatus of FIG. 1.

During analysis of the constituents, the valve 33 is closed, the valve 35 is open and the three-way valve 24 is set in the position shown in FIG. 2a, so that the gas flows, as carrier gas, through the line 35 to the chromatography column 5'. The column 5' is heated and the gas carries the volatile constituents substantially completely desorbed, through the column from the entry length thereof. After passing from the column 5', the gas enters a detector 37, from which, in known manner, signals are transmitted for processing in a recorded 38 and the production of a chromatogram.

In FIG. 1, by way of example, a cigarette 40 is shown impaled on the needle 27. As shown, the cigarette is enclosed within the tube with a wide peripheral clearance, but the arrangement may be such that its outer surface lies closer to the inside of the tube. When the body members 1 and 3 have been secured together and the valve 24 set for sampling (FIG. 2) and sufficient time has been allowed for the heaters 11 to have brought the interior of the member 3 to the selected temperature, stripper gas is directed into the tube 8 via the bore 28. The gas contacts the tobacco filling of the cigarette 40 by entering its ends, mainly the end remote from the mouth of the tube 8. Gas may also enter the cigarette through the paper wrapper thereof. The gas then flows, together with volatile constituents emanating from the cigarette 40, via the needle 27, valve 24 and needle 23 to the entry end of the column 5' which, during sampling, is at such a sub-ambient temperature as to trap the volatile constituents. Heat flow between the heated member 3 and the comparatively cool entry end of the column 5' or other parts of the chromatograph is restricted because the block 6 and bracket 4 are of heat-insulating materials. The sleeve 16 may serve to limit heat loss from the valve 24 and/or to radiate heat to that valve, so that condensation within the valve during sampling is prevented.

After the elapse of sufficient sampling time, the valve 24 is set to the position shown in FIG. 2a, the valve 33 is closed and the valve 35 is opened, so that the gas serves to carry the desorbed volatile constituents on through the column 5'. After analysis has commenced, the member 3 is removed from member 1 and the needle 27 is replaced by a flow restrictor, indicated at 27' in FIG. 2b. Finally the valve 24 is set to the position shown in FIG. 2b, in which a small proportion of the carrier-gas flow, limited by the restrictor 27', back-flushes the needle 23, the limbs 25 and 26 of the valve 24 and the bore 21 in the block 6. The third valve limb 24', fitted with the flow restrictor 24'', is also back flushed. The back-flushing removes any constituents from the sample which may have been deposited in the apparatus and which might otherwise contaminate a sample subsequently obtained by the apparatus.

The apparatus of FIG. 1 could be used for obtaining a headspace sample from solid materials other than a cigarette. For example, a solid sample such as a cigarette packet or loose tobacco could be placed in the sample tube 8 or a small amount of liquid could be smeared on the wall of the tube.

FIGS. 3 and 4 show a headspace-sampling apparatus designed to receive a cigarette packet of selected form. This apparatus comprises a first, generally disc-shaped body member 41 and a second, box-shaped, body member 42, each of the said members being made of brass.

At its right-hand end in FIG. 3, the member 42 has a flange 43 of the same diameter as the member 41.

Parts of a gas chromatograph are indicated by a broken line 44 in FIG. 3. The chromatograph includes two blocks 45 and 46. At diametrically opposed locations the body member 41 is mounted and secured to the blocks 45 and 46 by means of studs and nuts, as indicated at 45' and 46' in FIG. 4.

The body member 42 is releasably securable at its flange 43 to the body member 41 by nut and bolt fastenings 47. An 'O'-ring 48 between the member 41 and the flange 43 provides as hermetic seal. When the members 41, 42 are secured together, as shown in FIG. 3, they define a chamber 49 of only slightly larger dimensions than a cigarette packet. Thus, with the member 42 released from the member 41, a packet, indicated by broken lines 50 in FIG. 3, can be inserted into the member 42, which is then resecured to the member 41. The outer surfaces of the packet 50 then lie closely against the walls of the chamber 49. Clearances shown in FIG. 3 have been exaggerated for the sake of clarity.

Secured to the body member 41 are two guide rods 41' which extend perpendicularly to the member 41 and are receivable as a sliding fit in holes 43' (FIG. 4) in the flange 43 of the member 42. The member 41 has a boss 51 (FIG. 3) through which extends an open-ended bore 52 in which is received an end portion of a hollow needle 53 extending leftwards into the chamber 49 over a major portion of the length thereof. A first connection limb 54 of a three-way valve 55 is sealably received in the right-hand end of the needle 53, while a second limb 56 is sealably received in the entry end of a chromatography column 44' of the chromatograph 44.

On the outside of the left-hand end wall of the member 42, a boss 57 is brazed to that wall. There can be threadedly received in the boss 57 an end of a gas line (not shown) the other end of which is connected to a source of stripper gas. A short bore 58 connected the interior of the boss 57 to the chamber 49. A septum 59 is provided at the inner end of the interior of the boss 57 to seal the outer end of the bore 58. A second hollow needle, indicated in broken lines at 60, can be inserted into the chamber 49 through the septum and bore 58.

Heating means (not shown) may be arranged on the outside of the body member 42. With close contact between the packet 50 and the inner surfaces of the walls of the member 42, there will be good heat transfer to the interior of the packet 50. If such heating means is used, it may be associated with temperature control means, as in the case of the example previously described.

Figure 2B:
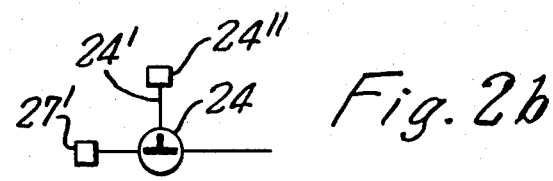

The gas flow circuitry associated with the sampling apparatus of FIGS. 3 and 4 may be similar to that described for the example of FIGS. 1 to 2b.

In use of the apparatus shown in FIGS. 3 and 4, the member 42 is released from the member 41 to permit the insertion of a packet, containing cigarettes, into the member 42. With the needle 53 in position, the member 42 is advanced, guided by the rods 41', towards the member 41, causing the needle 53 to penetrate the packet 50. The member 42 is then secured to the member 41. With the valve 55 in a position preventing communication via the needle 53 between the chamber 49 and the column 44', the second needle 60 is passed through the septum 59 and bore 58 to penetrate the packet 50. The gas line is connected to the boss 57 and stripper gas is caused to flow via the needle 60 to the interior of the packet 50. The valve 55 being turned to a position in which the bore of the needle 52 is in communication with the column 44', the gas can flow on through the needle 53 to the column 44'. The column is maintained at subambient temperature to trap, at its entry end, volatile constituents emanating from the interior of the packet 50.

After the elapse of sufficient sampling time, the valve 55 is set for analysis and carrier gas is supplied to the column 44'. The valve 55 can be back-flushed in a manner similar to that described for the previous example.

With either sampling apparatus, the third limb of the three-way valve can be utilised, when required, for the injection onto the chromatography column of other volatile substances for analysis.

This invention also comprises a method of headspace sampling wherein a substance the headspace of which is to be sampled in placed in a sample chamber defined by sampling body means comprising first passage means in communication with the entry end of a chromatography column held in operative position in a gas chromatograph and second passage means in communication with a source of gas, and a flow of said gas is established from said source, via the second passage means, the sample chamber and the first passage means, to said entry end of said column, whereby a headspace sample of said substance is swept directly on to an entry end region of said column, said headspace sample being cumulatively trapped at said region.

We claim:

1. Headspace-sampling apparatus comprising; sampling body means which defines a closable sample chamber, means for mounting said apparatus on a gas chromatograph with the sample chamber exterior to the chromatograph, a removably positioned solid sample in the chamber, first passage means extending substantially straight from said chamber to connection means for connecting said passage means, when the apparatus is so mounted, to the entry end of a chromatography column held in operative position in the gas chromatograph, a hollow needle the interior of which comprises part of said first passage means, means holding the needle in a stationary position within the closed sample chamber and the solid sample, which it penetrates, contained therein, second passage means extending to said chamber, and connection means for connecting a source of gas to said second passage means and providing a gas-flow path within the body means from the second-named connection means through the chamber, the sample and the first passage means including the needle to the first-named connection means.

2. Apparatus as claimed in claim 1 in which said body means comprises a first part mounted on the chromatograph by said mounting means, and a second part securable to the first part and releasable therefrom to give access to said chamber.

3. Apparatus as claimed in claim 1 wherein the form of said chamber is such that when a selected article, comprising a head-space to be sampled, is held in said chamber, the outer surface or surfaces of the article lie close against the inner wall or walls of said chamber.

4. Apparatus as claimed in claim 1 and further comprising heating means operable to heat said chamber.

5. Apparatus as claimed in claim 1 and further comprising valve means operable to close said first passage means.

6. Apparatus as claimed in claim 5, wherein said valve means comprises a three-way valve of which first and second connection limbs form respective portions of the first passage means and a third limb communicates with a gas-flow restrictor, the valve being adjustable between three positions, namely a first position in which portions of the first passage means upstream and downstream of the valve are in through-flow communication with each other and the flow restrictor is in communication with neither of said portions, a second position in which the downstream portion is in communication with the flow restrictor and the upstream portion is in communication with neither the downstream portion nor the flow restrictor, and a third position in which the two portions are in communication with each other and with the flow restrictor.

* * * * *